(12) United States Patent
Tanabe et al.

(10) Patent No.: US 8,951,230 B2
(45) Date of Patent: Feb. 10, 2015

(54) INDWELLING NEEDLE AND INDWELLING NEEDLE ASSEMBLY

(75) Inventors: Hidenori Tanabe, Tokyo (JP); Masao Kawamura, Tokyo (JP); Takato Murashita, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/447,700

(22) Filed: Apr. 16, 2012

(65) Prior Publication Data

US 2012/0197201 A1 Aug. 2, 2012

Related U.S. Application Data

(63) Continuation of application No. PCT/JP2010/068077, filed on Oct. 14, 2010.

(30) Foreign Application Priority Data

Oct. 16, 2009 (JP) .................................. 2009-238829

(51) Int. Cl.
*A61M 5/00* (2006.01)
*A61M 5/178* (2006.01)
(Continued)

(52) U.S. Cl.
CPC ............ *A61M 25/0606* (2013.01); *A61M 5/158* (2013.01); *A61M 39/0606* (2013.01); *A61M 2039/0633* (2013.01); *A61M 2039/0686* (2013.01)
USPC ........................ 604/167.03; 604/244; 604/249

(58) Field of Classification Search
USPC .................. 604/164.01–167.06, 158, 164.02, 604/168.01, 244, 246, 249
See application file for complete search history.

(56) References Cited

U.S. PATENT DOCUMENTS 4,016,879 A 4/1977 Mellor
5,242,411 A * 9/1993 Yamamoto et al. ...... 604/167.04
(Continued)

FOREIGN PATENT DOCUMENTS

DE 20 2007 006 190 U1 9/2007
EP 1 240 916 A1 9/2002
(Continued)

OTHER PUBLICATIONS

International Search Report (PCT/ISA/210) issued on Jan. 18, 2011, by Japanese Patent Office as the International Searching Authority for International Application No. PCT/JP2010/068077.

*Primary Examiner* — Matthew F Desanto
(74) *Attorney, Agent, or Firm* — Buchanan Ingersoll & Rooney PC (57) ABSTRACT

A indwelling needle includes an outer needle, an outer needle hub with a flow path communicating with the inside of the outer needle and configured to connect a connector to the flow path, and a valve mechanism which opens and closes the flow path. The valve mechanism includes a valve element in the middle of the flow path having an openable/closable opening/closing section and an operation member having a side hole and configured to open and close the opening/closing section. The valve mechanism is positionable in a state in which the operation member penetrates through the opening/closing section to protrude therefrom and the side hole is located closer to the front end side than the opening/closing section. When infusion liquid is supplied in this state, the liquid flows to the flow path through the side hole and the dead space within the flow path is filled with the infusion liquid.

19 Claims, 9 Drawing Sheets

(51) Int. Cl.
*A61M 25/06* (2006.01)
*A61M 5/158* (2006.01)
*A61M 39/06* (2006.01)

(56) References Cited

U.S. PATENT DOCUMENTS

| | | | |
|---|---|---|---|
| 8,357,119 B2 | 1/2013 | Stout et al. | |
| 8,361,020 B2 | 1/2013 | Stout | |
| 8,388,583 B2 * | 3/2013 | Stout et al. | 604/244 |
| 2002/0128604 A1 | 9/2002 | Nakajima | |
| 2005/0267400 A1 | 12/2005 | Haarala et al. | |
| 2007/0083162 A1 | 4/2007 | O'Reagan et al. | |
| 2007/0100295 A1 * | 5/2007 | Belley et al. | 604/246 |
| 2009/0177163 A1 * | 7/2009 | King et al. | 604/167.03 |
| 2010/0204648 A1 * | 8/2010 | Stout et al. | 604/122 |
| 2011/0160662 A1 | 6/2011 | Stout et al. | |
| 2011/0160663 A1 | 6/2011 | Stout et al. | |

FOREIGN PATENT DOCUMENTS

| | | |
|---|---|---|
| JP | 11-128359 A | 5/1999 |
| JP | 2002-263197 A | 9/2002 |
| JP | 2007-521926 A | 8/2007 |
| WO | 2007/044878 A2 | 4/2007 |
| WO | 2010/093791 A1 | 9/2010 |

* cited by examiner

INDWELLING NEEDLE AND INDWELLING NEEDLE ASSEMBLY

This application is a continuation of International Application No. PCT/JP2010/068077 filed on Oct. 14, 2010, and claims priority to Japanese Application No. 2009-238829 filed on Oct. 16, 2009, the entire content of both of which is incorporated herein by reference.

TECHNICAL FIELD

The present invention relates to a indwelling needle and a indwelling needle assembly that includes such indwelling needle.

BACKGROUND DISCUSSION

At the time of infusion into a patient or in other similar situations, an indwelling needle assembly connected to an infusion line is used to puncture a patient's blood vessel and is left placed there.

Such an indwelling needle assembly includes a hollow outer needle, an outer needle hub firmly attached to the proximal end of the outer needle, an inner needle having a sharp needle point at the distal end thereof and inserted in the outer needle, and an inner needle hub firmly attached to the proximal end of the inner needle. An example is disclosed in Japanese Application Publication No. 2002-263197. In addition, in the outer needle hub are contained a valve element (stanching valve), and an operation member (pusher) which operates the opening and closing of the valve element.

At the time of puncturing a patient's blood vessel by the indwelling needle assembly, the puncturing operation is conducted in an assembled state (see FIG. 1 of the above-cited Japanese application publication) in which the inner needle is inserted in the outer needle and the needle point of the inner needle is protruded from the distal end of the outer needle. Then, when the needle point of the inner needle reaches the inside of the blood vessel, blood having flowed in through an opening at the needle point flows through the inner cavity of the inner needle into the inside of the transparent inner needle hub (flashback). This makes it possible to confirm (visually check) the fact that the inner needle has arrived in the blood vessel. When this flashback is confirmed, the outer needle is advanced, and the outer needle is inserted in the blood vessel.

Next, while gripping the outer needle by hand, the inner needle is drawn out of the outer needle (see FIG. 2 of the above-cited Japanese application publication). As a result, placement of the outer needle in the blood vessel can be achieved. Besides, in this instance, the valve element in the outer needle hub is in a closed state, so that leakage of blood is prevented.

Subsequently, a tubular connector (tube) is connected to a proximal portion of the outer needle hub (see FIG. 3 of the above-cited Japanese application publication). By the connector thus connected, the operation member inside the outer needle hub is pushed in the distal direction, to push open the valve element. Consequently, the valve element is put into an open state, so that an infusion liquid can be administered from the connector side to the outer needle side.

Meanwhile, the operation member pressed by the connector is set in a state in which its distal portion is protruded to the distal side relative to the valve element (see FIG. 3 of the above-cited Japanese application publication). When the infusion liquid is administered in this state, a part surrounded by a wall portion defining a flow path and an outer circumferential portion of a distal portion of the operation member that is protruding from the valve element becomes a dead angle, so that the infusion liquid cannot go around into the part. Accordingly, blood is left stagnating in the part. Thus, there has been a problem that the stagnating blood becomes a source of bacterial proliferation or a source of thrombus.

SUMMARY

The disclosed indwelling needle and indwelling needle assembly are configured so that when blood flows into the flow path of a hub by flashback and thereafter the flow path is primed with a liquid, the blood does not stagnate in the flow path, particularly in a part surrounded by a wall portion defining the flow path and an outer circumferential portion of a protruding part of an operation member protruding from an opening/closing section of a valve element.

The indwelling needle includes: a hollow outer needle possessing an inside; a hub provided at a proximal portion of the outer needle, having a flow path communicatable with the inside of the outer needle and configured to connect a tube body to the flow path; and a valve mechanism which closes and opens the flow path. The valve mechanism includes: a valve element provided at an intermediate portion of the flow path, with the valve element being made of elastic material and having an opening/closing section which can be opened and closed; and an operation member which operates the opening and closing of the opening/closing section, the operation member possessing a tubular shape and having at least one side hole penetrating a wall of the operation member. The valve mechanism is positionable in a first state in which the opening/closing section is closed and the operation member is located proximally relative to the opening/closing section, and is positionable in a second state in which the operation member penetrates through the opening/closing section to protrude from the opening/closing section. The side hole is located distally relative to the opening/closing section, as a result of distal movement of the operation member pressed by the tube body upon connection of the tube body to the flow path starting from the first state, and when a liquid is supplied from the tube body in the second state, the liquid flows out from the inside of the operation member into the flow path through the side hole, and a part of the flow path which is surrounded by a wall portion defining the flow path and an outer circumferential portion of a protruding part of the operation member protruding from the opening/closing section is filled with the liquid having flowed out through the side hole.

The indwelling needle can be configured to include a plurality of the side holes circumferentially arranged around the operation member.

The side hole can also be configured so that it opens also to the distal end surface of the operation member.

The operation member can be configured to have a distal opening which opens in the distal end surface thereof, wherein the side hole has an aperture diameter of not less than 10% of the inside diameter of the distal opening of the operation member.

The side hole preferably has an area of not less than 0.04 mm$^2$.

The operation member can be outfitted with an auxiliary part which assists movement toward the side hole of the liquid having passed through the inside thereof.

The opening/closing section is preferably comprised of a plate-shaped part, and a through-hole penetrating the plate-shaped part in the thickness direction of the plate-shaped part.

The operation member can also be configured to include an engagement section which engages the opening/closing section in the second state.

The engagement section can include a ring-shaped projecting part formed at an outer circumferential portion of the operation member along the circumferential direction of the latter.

The side hole can be arranged to open in the projected part.

The operation member can be configured to include a reduced diameter section where its inside diameter is reduced, with the side hole opening in the reduced diameter section.

Another aspect of the disclosure here involves an indwelling needle assembly that includes the indwelling needle described above and an inner needle positioned in the outer needle when the indwelling needle is in the first state, and wherein blood flows through the outer needle into the flow path when the inner needle is made to puncture a living body surface.

According to another aspect, an indwelling needle comprises: a hollow outer needle possessing an inside; a hub connected to a proximal portion of the outer needle and extending proximally beyond a proximal-most end of the outer needle, with the hub possessing an open proximal end to receive a portion of a tube body, and the hub including a flow path surrounded by a wall of the hub and fluidly communicatable with the inside of the outer needle; a valve element positioned in the hub at an intermediate portion of the flow path; and an operation member possessing a distal end, a proximal end, an outer circumferential surface and a through hole extending throughout the operation member from a distal opening which opens to the distal end of the operation member and a proximal opening which opens to a proximal end of the operation member, with the operation member also including a side hole communicating with the through hole and opening to the outer circumferential surface of the operating member. The valve element is made of elastic material and includes an openable and closable opening/closing section, and the operation member is positioned inside the hub in an initial position so that the side hole of the operation member is located proximally of the valve element. The opening/closing section is in a closed state when the operation member is positioned inside the hub so that the side hole of the operation member is proximally spaced from the valve element. The operation member in the initial position in the hub is movable to a forward shifted position, when the portion of the tube body is positioned in the hub, in which the operation moves toward the valve and passes through the opening/closing section so that the side hole of the operation member is distal of the opening/closing section while the proximal end of the operation member is proximal of the opening/closing section to permit liquid introduced into the proximal opening of the through hole from the tube body to flow along the through hole and to flow out of the through hole by way of both the distal opening and the side hole so that the liquid flowing out of the side hole fills a part of the flow path surrounded by a portion of the wall of the hub and the outer circumferential surface of a part of the operation member protruding distally beyond the opening/closing section.

Another aspect of the disclosure here involves a method of using an indwelling needle. The method comprises: puncturing skin of a living body with an inner needle positioned inside a hollow outer needle, with the hollow outer needle being connected a hub having a flow path, and a valve element positioned at an intermediate portion of the flow path, and the valve element having an opening/closing section through which the inner needle extends so that a portion of the inner needle is on a distal side of the valve element and a portion of the inner needle is on a proximal side of the valve element; positioning the outer needle, following the puncturing of the skin of the living body with the inner needle, to penetrate the skin of the living body so that blood from the living body flows into the flow path of the hub by way of a space between an inner surface of the outer needle and an outer surface of the inner needle; removing the inner needle from within the outer needle, with the opening/closing section of the valve element automatically closing upon removal of the inner needle; and moving a tubular operation member positioned in the hub in a forward direction toward the valve member. The tubular operation member possesses a side hole which opens to the outer circumferential surface of the operation member and which communicates with the inside of the tubular operation member. The method further comprises continuing to move the tubular operation member in the forward direction so that the tubular operation member penetrates through the opening/closing section; stopping the movement of the tubular operation member in the forward direction when the side hole is positioned distally of the opening/closing section and while a portion of the tubular operation member is proximal of the opening/closing section; and introducing liquid into the inside of the tubular operation member through a proximal opening at the proximal end of the operation member, with at least some of the liquid flowing into the side hole and flowing out of the side hole at the outer circumferential surface of the tubular operation member so that a part of the flow path surrounded by a wall portion defining the flow path and an outer circumferential portion of a protruding part of the operation member protruding distally from the opening/closing section is filled with the liquid which has flowed out through the side hole.

DETAILED DESCRIPTION

Set forth below with reference to the accompanying drawing figures is a detailed description of the indwelling needle and the indwelling needle assembly disclosed here.

FIGS. 1-8 illustrate aspects of a first embodiment of the indwelling needle and indwelling needle assembly disclosed here as examples of the disclosed indwelling needle and indwelling needle assembly. In the following description, for convenience, the right side in FIGS. 1 to 6 and 8 (and in FIG. 12, as well) will be referred to as "proximal," and the left side as "distal;" similarly, the right upper side in FIG. 7 (and in FIGS. 9 to 11, as well) will be referred to as "proximal," and the left lower side as "distal."

Figure 1:
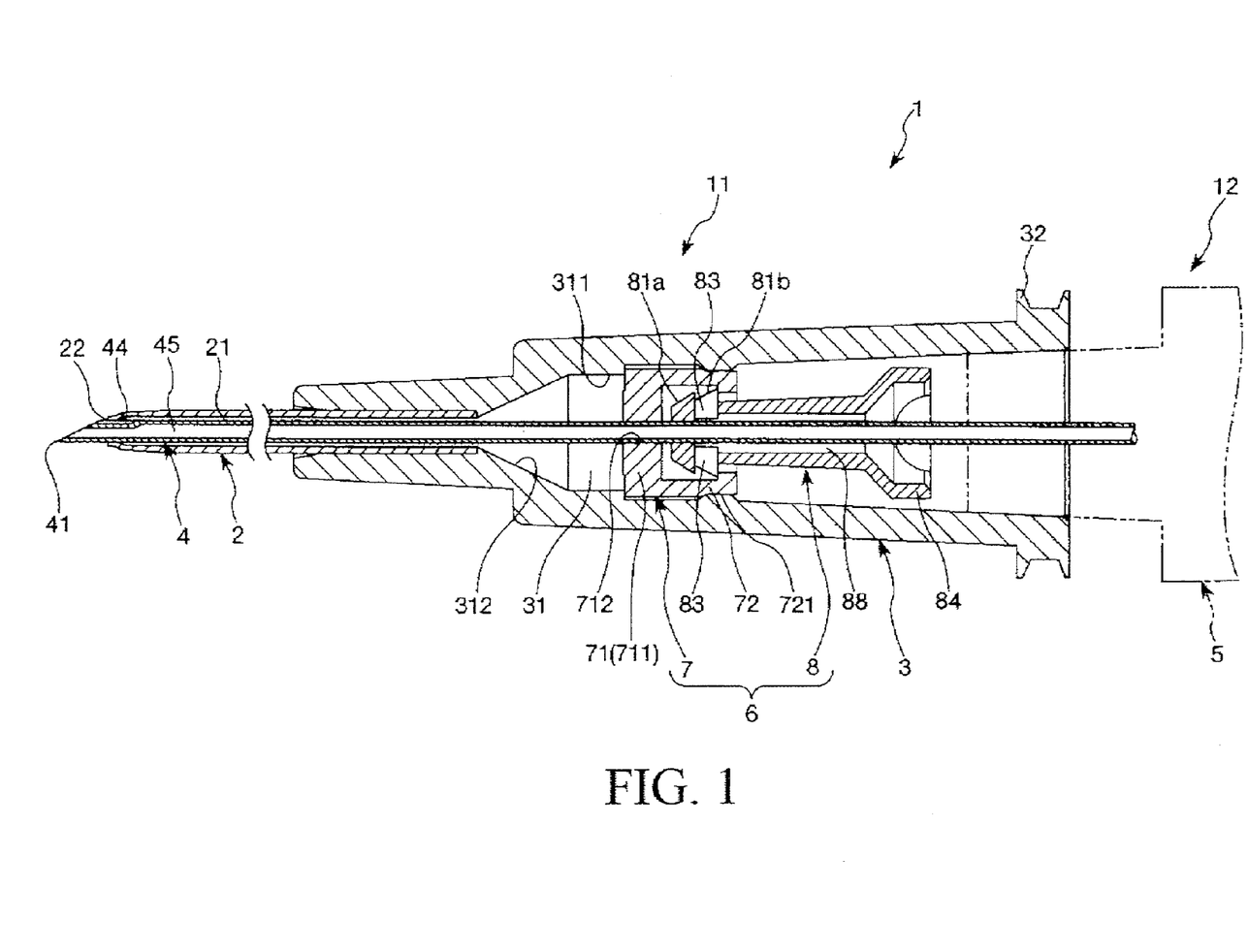
FIG. 1 is a longitudinal sectional view showing a first embodiment of the indwelling needle assembly (indwelling needle) disclosed here by way of example.

An indwelling needle assembly 1 shown in FIG. 1 is made up of a indwelling needle 11 and a puncture needle (puncture means) 12. The indwelling needle assembly 1 can take an assembled state (the state shown in FIGS. 1 and 2) in which the indwelling needle 11 and the puncture needle 12 are assembled, and a disassembled state (the state shown in FIGS. 3 to 6) in which the puncture needle 12 has been pulled out of the indwelling needle 11. The indwelling needle assembly 1 can puncture a living body surface when in the assembled state. Thereafter, the indwelling needle assembly 1 is disassembled, whereby the indwelling needle 11 can be left placed at the living body surface. In addition, a connector 20 can be connected to the indwelling needle 11 left placed at the living body surface (see FIGS. 4 to 6).

Before describing the indwelling needle assembly 1, the connector 20 will be described.

Figure 4:
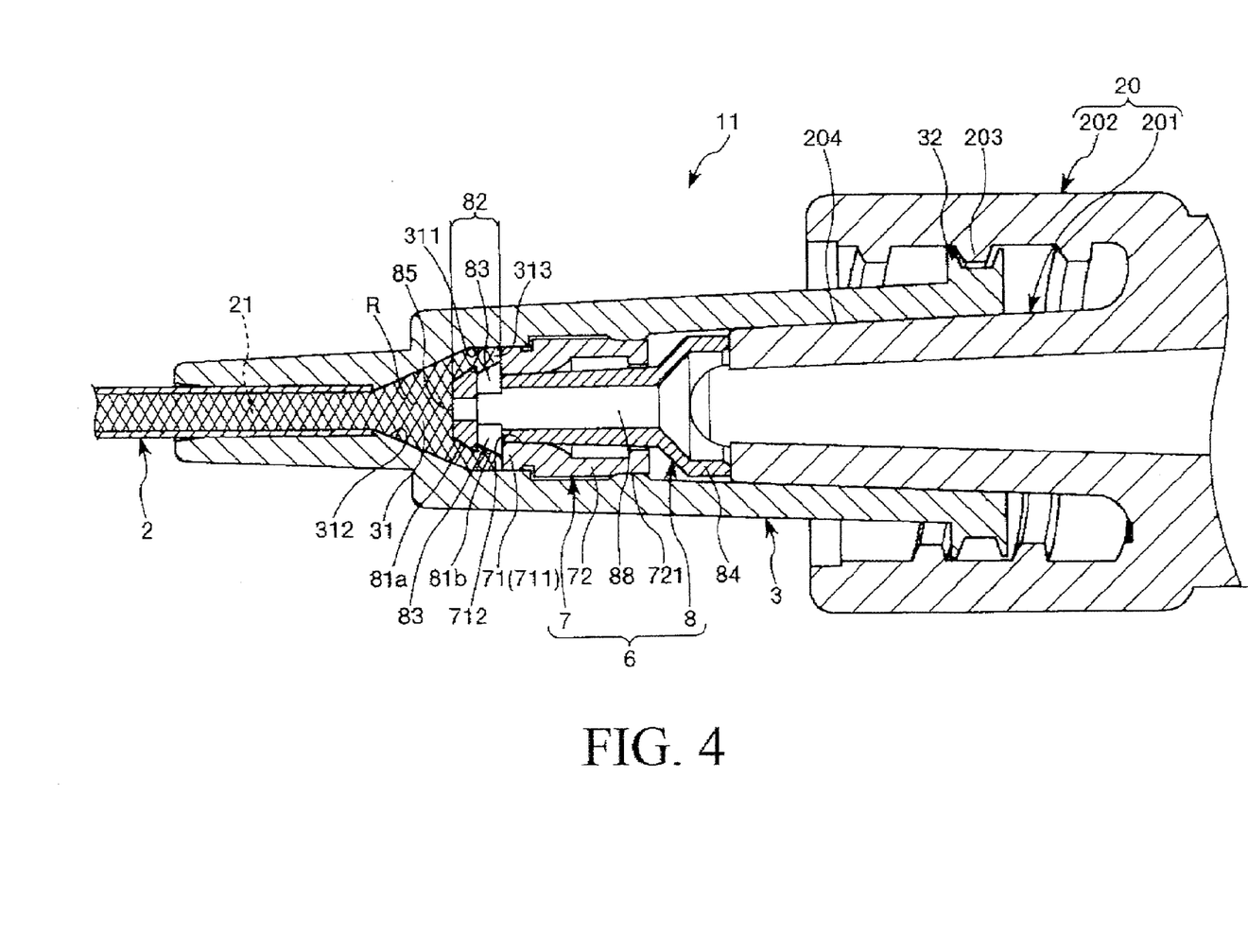
FIG. 4 is a longitudinal sectional view sequentially illustrating the states in use of the indwelling needle assembly shown in FIG. 1.
Figure 5:
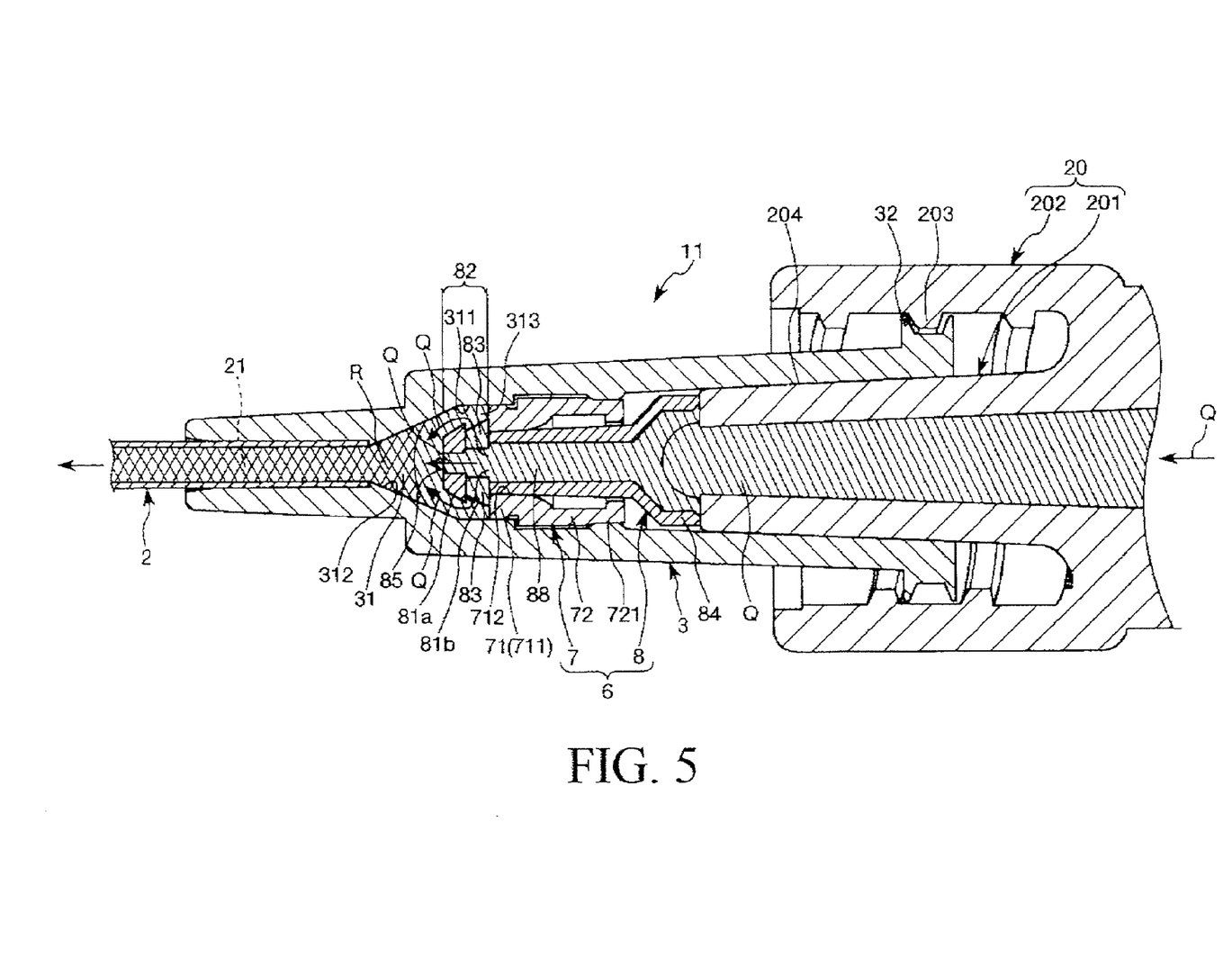
FIG. 5 is a longitudinal sectional view sequentially illustrating the states in use of the indwelling needle assembly shown in FIG. 1.
Figure 6:
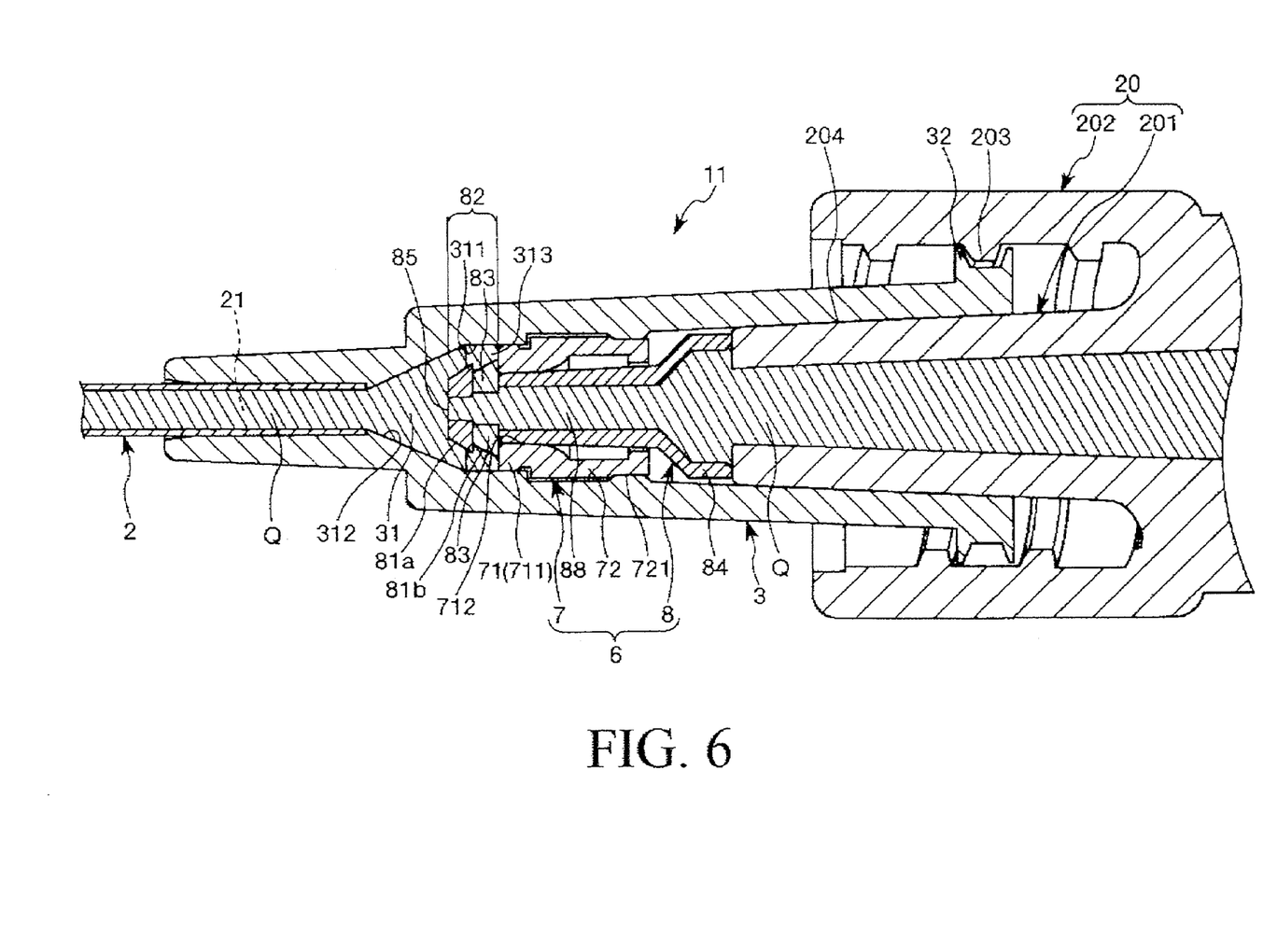
FIG. 6 is a longitudinal sectional view sequentially illustrating the states in use of the indwelling needle assembly shown in FIG. 1.

As shown in FIGS. 4 to 6, the connector 20 is one that is connected to a proximal portion of the indwelling needle 11. This connector 20 has a circular or cylindrical tube-shaped connector main body (tube body) 201, and a lock section 202 provided on the outer circumference side of (radially outwardly of) the connector main body 201.

The connector main body 201 has a tapered shape in which its outside diameter gradually decreases along the distal direction. This enables the connector main body 201 to be relatively easily inserted into the proximal portion of the indwelling needle 11 at the time of connecting the connector 20, so that the connecting operation can be performed rather easily.

The lock section 202 is a tubular section which is disposed concentrically with the connector main body 201. The lock section 202 is provided with a female screw 203 at an inner circumferential portion thereof. The female screw 203 can make screw engagement with a male screw 32 at an outer circumferential surface of an outer needle hub 3 of the indwelling needle 11 which will be described later. The screw engagement between these screws ensures that the connected state of the connector 20 and the indwelling needle 11 can be maintained relatively assuredly. In other words, these members can be securely inhibited or prevented from unwillingly disengaging from each other. While the lock section 202 is formed integrally with the connector main body 201 in the configuration shown in the drawings, the invention is not limited in this regard, and the lock section 202 may be configured as a body separate from the connector main body 201.

In addition, a distal portion of a tube (not shown) is connected to a proximal portion of the connector 20. A bag (not shown) filled with an infusion liquid (liquid) Q is connected to a proximal portion of the tube. The indwelling needle 11, in the connected state in which the connector 20 is connected thereto, is supplied with the infusion liquid from the bag (see FIGS. 5 and 6).

Now, the indwelling needle assembly 1 will be described below.

As shown in FIGS. 1 to 6, the indwelling needle 11 has a hollow outer needle 2, with the outer needle hub 3 fixed to a proximal portion of the outer needle 2, and a valve mechanism 6 which closes and opens a flow path 31 in the outer needle hub 3.

The outer needle 2 is preferably one that has a certain degree of flexibility. The material constituting the outer needle 2 is preferably a resin material, particularly a soft resin material. Specific examples of the material include fluororesins such as PTFE, ETFE, PFA, etc., olefin resins such as polyethylene, polypropylene, etc. and their mixtures, polyurethane, polyesters, polyamides, polyether nylon resin, and mixtures of any of the olefin resins with an ethylene-vinyl acetate copolymer.

The outer needle 2 as above preferably has inside visibility along a portion of its length or along its entire length. In other words, the outer needle 2 is preferably composed of a transparent (colorless transparent), colored transparent or semi-transparent resin. This helps ensure that when the outer needle 2 has arrived in a blood vessel, flashback of blood R flowing in through a distal opening 22 of the outer needle 2 can be visually confirmed.

In addition, the material constituting the outer needle 2 may contain a radiopaque agent, for example, barium sulfate, barium carbonate, bismuth carbonate or tungstic acid blended therein, whereby a radioscopic contrast function can be imparted to the outer needle 2.

As shown in FIG. 1 (and in FIGS. 2 to 6, as well), the outer needle hub 3 is firmly attached (fixed) to a proximal portion of the outer needle 2 in a liquid-tight manner by such a method as caulking, fusing (heat fusing, high-frequency fusing) or adhesion using an adhesive.

The outer needle hub 3 is composed of a circular or cylindrical tube-shaped member, and its inner cavity functions as the flow path 31. The flow path 31 communicates with the inner cavity 21 of the outer needle 2. In addition, the valve mechanism 6 is contained and arranged in the flow path 31. Thus, the outer needle hub 3 has a configuration in which the inner cavity portion thereof is utilized not only as the flow path 31 but also as a containing section for containing the valve mechanism 6.

At a distal portion of the flow path 31, a tapered section 312 is formed in which the inside diameter of a wall portion 311 defining the flow path 31 gradually decreases along the distal direction. This helps ensure that the infusion liquid Q having flowed down the flow path 31 along the distal direction is relatively easily guided into the inner needle 2.

In the outer needle hub 3 is contained the valve mechanism 6. The valve mechanism 6 is for closing and opening the flow path 31, and includes a valve element 7 and an operation member 8 which operates the opening/closing of the valve element 7.

As shown in FIG. 1, the valve element 7 is disposed at an intermediate portion of the flow path 31. The valve element 7 is formed from an elastic material, and has an opening/closing section 71 which can be opened and closed, and a fixation section 72 which is fixed relative to the flow path 31.

The opening/closing section 71 includes a circular disk-like plate-shaped part 711, and a through-hole 712 formed in the plate-shaped part 711. The plate-shaped part 711 is in such a posture that its surface is perpendicular to the longitudinal direction of the flow path 31. In addition, the through-hole 712 is composed, for example, of a slit which penetrates the plate-shaped part 711 in the thickness direction of the latter. The shape of the slit is not specifically restricted; for example, the slit shape may be a straight line segment shape, a cross shape, a Y-shape (the shape of katakana "ト") or the like. Such a configuration helps ensure that the opening/closing section 71 is an assuredly self-closing section. That is, the opening/closing section is normally open in the absence of the operation member penetrating the opening/closing section.

The fixation section 72 is formed integrally with the opening/closing section 71. The fixation section 72 is a tubular section projecting in a proximal direction from an edge portion of the opening/closing section 71 (the plate-shaped part 711). A part of the whole part of an outer circumferential portion 721 of the fixation section 72 is fitted to a wall portion 311 of the flow path 31, whereby the valve element 7 is fixed relative to the flow path 31.

The elastic material constituting the valve element 7 is not particularly limited. Examples of the material include various elastic materials such as various rubber materials (particularly, vulcanized ones) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene or the like, and mixtures thereof. Among these elastic materials, particularly preferred for use here is isoprene rubber. The use of isoprene rubber as the material for forming the valve element 7 is advantageous in that the valve element 7 shows a relatively low compressive permanent set and the product shows a longer useful life.

The operation member 8 is a member which operates the opening/closing of the opening/closing section 71 of the valve element 7. The operation member 8 is so supported as to be movable along the longitudinal direction of the flow path 31. This enables the indwelling needle 11 (the valve mechanism 6) to take a first state in which the operation member 8 is located on the proximal side relative to the opening/closing section 71 (see FIGS. 1 to 3) and a second state in which the operation member 8 is moved in the distal direction, starting from the first state, to penetrate the opening/closing section 71 and to protrude from the opening/closing section 71 (see FIGS. 4 to 6). In the first state, the opening/closing section 71 is closed by a self-closing property of the opening/closing section 71. As a result of this, the flow path 31 is closed. In the second state, the opening/closing section 71 has been forcibly opened by the penetration of the operation member 8 therethrough. As a result of this, the flow path 31 is in such a state that the distal side thereof and the proximal side thereof communicate with each other through the valve mechanism 6.

Figure 7:
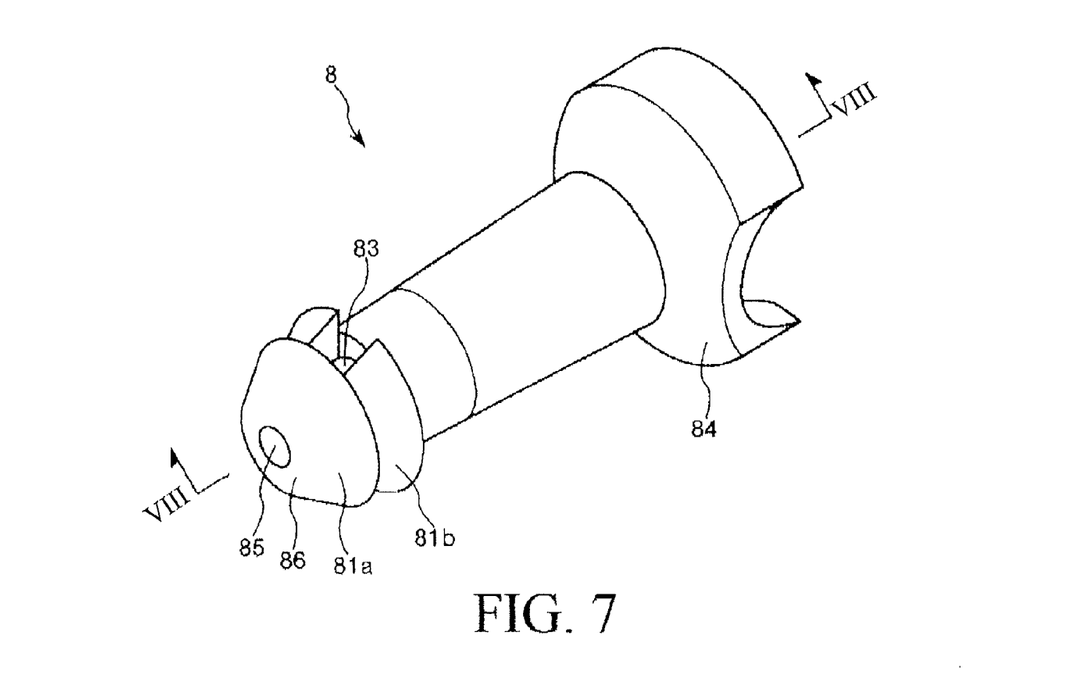
FIG. 7 is a perspective view of an operation member (first embodiment) possessed by the indwelling needle assembly.
Figure 8:
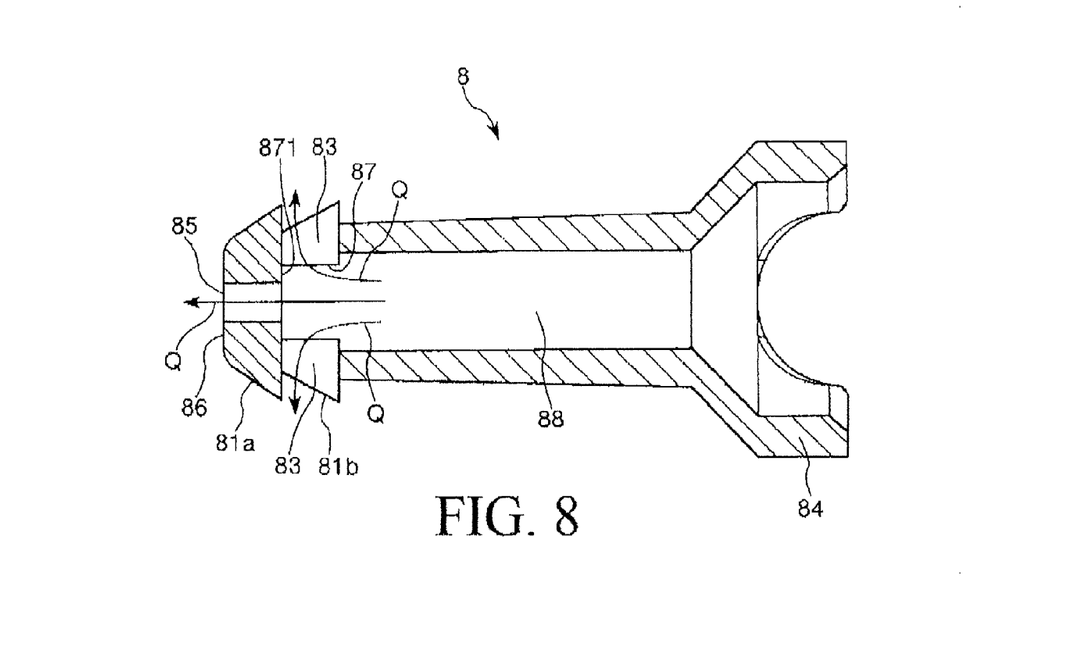
FIG. 8 is a sectional view taken along the section line VIII-VIII in FIG. 7.

As shown in FIGS. 7 and 8, the operation member 8 is composed of a circular or cylindrical tube-shaped member. When the operation member 8 moves, an outer circumferential portion of the operation member 8 slides on the wall portion 311 of the flow path 31, so that the movement is performed rather stably.

The operation member 8 is formed at an outer circumferential portion of the proximal end thereof with a proximal enlarged diameter section 84 where its inside diameter is enlarged. The inside diameter of the proximal enlarged diameter section 84 is greater than the inside diameter of the connector main body 201 of the connector 20. This helps ensure that in the connected state the infusion liquid Q can flow from the connector main body 201 into the operation member 8 relatively easily and assuredly (see FIG. 5).

The operation member 8 is formed at an outer circumferential portion of the distal end thereof with two distal enlarged diameter sections (projecting sections) 81a and 81b at which its outside diameter is enlarged, in other words which project outwardly along its circumferential direction. Of these distal enlarged diameter sections 81a and 81b, the distal enlarged diameter section 81b functions as an engagement section which engages with the opening/closing section 71 of the valve element 7 in the second state. With the engagement of the distal enlarged diameter section 81b with the opening/closing section 71 of the valve element 7, the operation member 8 is prevented from unwillingly moving in the proximal direction, so that the second state is maintained securely. Side holes 83 in the operation member 8 which will be described later can be exposed to (can front on) the inside of the flow path 31 relatively assuredly.

In addition, the distal enlarged diameter sections 81a and 81b each have a tapered shape. This helps ensure that when the operation member 8 penetrates the opening/closing section 71 of the valve element 7, the distal enlarged diameter sections 81a and 81b can relatively securely push open the opening/closing section 71 outward in this order. Therefore, the penetration is performed rather easily. That part (the distal enlarged diameter sections 81a and 81b) of the operation member 8 which penetrates the opening/closing section 71 protrudes from the opening/closing section 71. Hereafter, this protruding part will be referred to as "the protruding part 82."

Two side holes 83 open at the distal enlarged diameter section 81b (the protruding part 82). The side holes 83 each pierce through a side wall (tube wall) of the operation member 8. In addition, the side holes 83 are each tetragonal in shape in side view. As shown in FIGS. 5 and 6, in the second state, the protruding part 82 of the operation member 8 protrudes from the opening/closing section 7, so that the side holes 83 are located on the distal side relative to the opening/closing section 71 of the valve element 7. When the infusion liquid Q is supplied from the connector 20 in this state, the infusion liquid Q passes through the inside of the operation member 8, and part of the liquid can flow out into the flow path 31 through the side holes 83.

Figure 2:
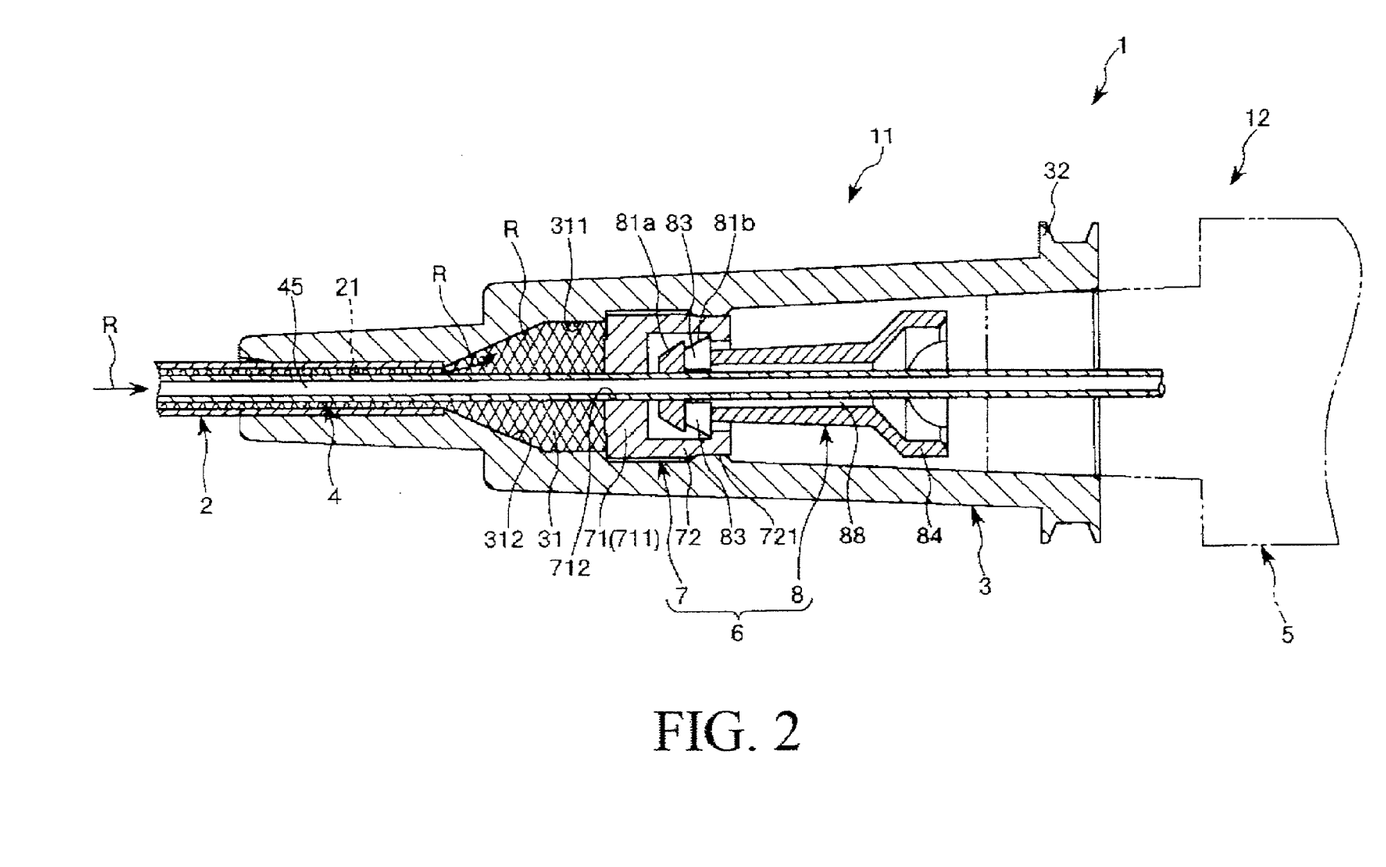
FIG. 2 is a longitudinal sectional view sequentially illustrating the states in use of the indwelling needle assembly shown in FIG. 1.

When the indwelling needle assembly 1 in the assembled state punctures a living body surface as above-mentioned and the outer needle 2 arrives in a blood vessel, blood R flows into the flow path 31 through the distal opening 22 of the outer needle 2 (see FIG. 2). The blood R thus having flowed in is left as it is in the flow path 31 even in the disassembled state (see FIG. 3). Then, when the connector 20 is connected to the indwelling needle 11, the indwelling needle 11 shifts into the second state (see FIG. 4), resulting in that the infusion liquid Q can be administered into the living body (see FIGS. 5 and 6).

Meanwhile, if the side holes 83 in the operation member 8 are omitted, administration of the infusion liquid Q in the second state would result in the part the inside of the flow path 31 which is surrounded by the wall portion 311 and an outer circumferential portion of the protruding part 82 of the operation member 8 becoming a dead space (dead angle) 313, and the infusion liquid Q having flowed out through the distal opening 85 of the operation member 8 cannot come around into the dead space 313. Therefore, the blood R would be left stagnating in the dead space 313. Thus, there is a problem that the blood R thus left stagnating may become a source of bacterial proliferation or a source of thrombus.

In the indwelling needle here, however, the operation member 8 is formed with the side holes 83. This helps ensure that the side holes 83 front on the dead space 313 in the second state, so that the blood R in the dead space 313 is securely replaced by (discharged by) the infusion liquid Q having flowed out through the side holes 83. Accordingly, the blood R can be relatively securely prevented from stagnating in the dead space 313, so that the above-mentioned problem can be solved.

In addition, the side holes 83 are arranged at regular intervals along the circumferential direction of the operation member 8, or arranged on the opposite sides, with the center axis of the operation member 8 therebetween. This helps relatively evenly distribute the infusion liquid Q through the side holes 83 to the whole region of the dead space 313, so that the blood R in the dead space 313 can be replaced by the infusion liquid Q more assuredly.

Then side holes 83 each have a hole diameter of preferably not less than 10%, more preferably 40 to 120%, of the inside diameter of the distal opening 85.

The side holes 83 each have an area of preferably not less than 0.04 mm$^2$, more preferably 0.15 to 1.7 mm$^2$.

With the size of each of the side holes 83 set within the above-mentioned numerical range, the infusion liquid Q can be made to flow out through the side holes 83 relatively assuredly, so that the inside of the dead space 313 can be replaced with the blood R more securely.

The side holes 83 may be equal or different in size.

As shown in FIG. 8, the operation member 8 is formed at an inner circumferential portion of the distal end thereof with a reduced diameter section 87 where its inside diameter is reduced stepwise. The operation member 8 is formed at the inner circumferential portion of the distal end thereof with the reduced diameter section 87 where its inside diameter is reduced, and the reduced diameter section 87 and a distal opening 85 smaller than it in inside diameter form a stepped part 871. There may also be adopted a structure in which the reduced diameter section 87 is omitted and in which an inner circumferential portion of the distal end of the operation member 8 and a distal opening 85 smaller than it in inside diameter form a stepped part 871. In addition, the side holes 83 open on the proximal side relative to the stepped part 871. Such a configuration helps ensure that a portion of the infusion liquid Q having flowed down through an inner cavity part (the inside or through hole) 88 of the operation member 8 collides on the stepped part 871, and is changed in flow direction to the sides of the side holes 83. The infusion liquid Q thus changed in flow direction can flow out through the side holes 83 rather assuredly. Thus, in the operation member 8, the stepped part 871 functions as an auxiliary part by which the infusion liquid Q is assisted in flowing toward the side holes 83.

As shown in FIG. 1, the puncture needle 12 has the inner needle 4, and the inner needle hub 5 fixed to a proximal portion of the inner needle 4. In the assembled state, the inner needle 4 is inserted in the outer needle 2, and a distal portion of the inner needle hub 5 is inserted and fitted in the outer needle hub 3. In this case, the indwelling needle 11 is in the first state, in which the inner needle 4 is inserted in and passed through the valve element 7 and the operation member 8 collectively.

The inner needle 4 has a sharp needle point 41 at the distal end thereof. The length of the inner needle 4 is set to such a value that at least the needle point 41 protrudes from the distal opening 22 of the outer needle 2 in the assembled state. By way of the needle point 41, a living body surface can be punctured.

The inner needle 4 may be a solid needle, but it is preferably a hollow needle. In the case where the inner needle 4 is a hollow needle, blood flows into a hollow part 45 of the inner needle 4 upon puncture of a blood vessel by the inner needle 4, whereby flashback of the blood R can be confirmed.

In the case where the inner needle 4 is a solid needle, sufficient strength can be secured while reducing the outside diameter thereof. In addition, when the inner needle 4 is a solid needle, at the time of discarding the puncture needle 12 after operation, there is no danger of remaining of the blood inside the inner needle 4 or flow-out of the remaining blood, so that high safety is secured.

In addition, the inner needle 4 may have a configuration in which it has both a hollow part and a solid part (for example, a configuration in which the inner cavity of a hollow needle is partly filled up so that the needle is hollow on the distal side and solid on the proximal side). With the inner needle 4 as a whole composed of a single member, however, a reduction in the cost of the inner needle 4 can be realized.

The inner needle 4 is formed at an outer circumferential portion thereof with a groove (flow path) 44 in a recessed form along the longitudinal direction of the inner needle 4. The groove 44 functions as a guide path which, upon puncture of a blood vessel, guides blood R into the inner cavity 21 of the outer needle 2. The blood R guided through the groove 44 flows into a gap between the outer surface of the inner needle 4 and the inner surface of the outer needle 2. This enables flashback of the blood R to be securely confirmed from an early stage. Then, the blood R flows through the inner cavity 21 of the outer needle 2 into the flow path 31 in the outer needle hub 3 (see FIG. 2).

Examples of the material constituting the inner needle 4 include metallic materials such as stainless steel, aluminum, aluminum alloys, titanium and titanium alloys.

The inner needle hub 5 is firmly attached (fixed) to a proximal portion of the inner needle 4. In addition, the inner needle hub 5 is tubular in shape, and an air filter (not shown) is disposed at an opening portion of the proximal end of the inner needle hub 5.

The inner needle hub 5 as above and the above-mentioned outer needle hub 3 are each preferably formed from a transparent (colorless transparent), colored transparent or semi-transparent resin, to secure inside visibility. This helps ensure that when the outer needle 2 arrives in a blood vessel, flashback of the blood R flowing in through the groove 44 of the inner needle 4 as above-mentioned can be visually confirmed.

The materials constituting the outer needle hub 3, the inner needle hub 5 and the operation member 8 are not specifically restricted. Examples of the materials include various resin materials such as polyolefin such as polyethylene, polypropylene, ethylene-vinyl acetate copolymer, etc., polyurethane, polyamides, polyesters, polycarbonates, polybutadiene, and polyvinyl chloride.

Now, the states in used of the indwelling needle assembly 1 will be described below.

[1] The indwelling needle assembly 1 is set into an assembled state as shown in FIG. 1. Here, the operation member 8 is in an initial position in which the side hole(s) 83 are positioned proximal of the valve element (opening/closing section).

In addition, an infusion bag filled with an infusion liquid Q is preliminarily connected to the connector 20, so that the infusion liquid Q can be supplied.

[2] Next, the indwelling needle assembly 1 in the assembled state is gripped, and a patient's blood vessel (vein or artery) is punctured using the sharp needle point 41. When the outer needle 2 arrives in the blood vessel, the inside pressure of the blood vessel (blood pressure) causes the blood R to flow back in the proximal direction through the groove 44 of the inner needle 4 and in the inner cavity 21 of the outer needle 2, so that this situation can be confirmed at the outer needle 2 or the outer needle hub 3 which has inside visibility (see FIG. 2). After this situation is confirmed, the indwelling needle assembly 1 is further advanced by a very small distance in the distal direction.

As shown in FIG. 2, the blood R flowing back reaches that part of the flow path 31 at which the valve element 7 is located.

Figure 3:
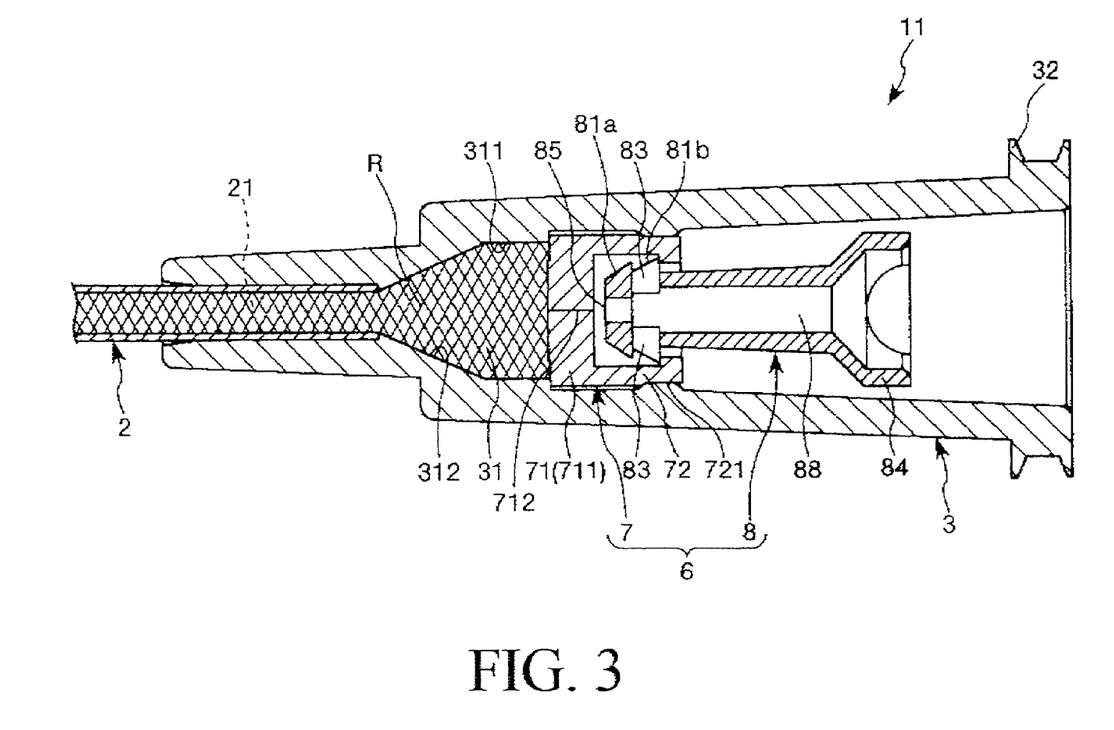
FIG. 3 is a longitudinal sectional view sequentially illustrating the states in use of the indwelling needle assembly shown in FIG. 1.

[3] When the outer needle 2 has arrived in the blood vessel, the outer needle 2 or the outer needle hub 3 is fixed by one hand, and the inner needle hub 5 is gripped by the other hand and pulled in the proximal direction, to pull the inner needle 4 out of the outer needle 2 (see FIG. 3). As a result, the indwelling needle assembly 1 is set in the disassembled state. In this instance, in the indwelling needle 11, the valve element 7 is in a closed state, so that the blood R in the flow path 31 is prevented from leaking out to the exterior. In addition, the puncture needle 12 pulled off is useless and is therefore discarded.

[4] Subsequently, the outer needle hub 3 of the indwelling needle 11 is fixed to the skin with a pressure sensitive adhesive tape or the like. Then, the connector 20 is connected to the outer needle hub 3 (see FIG. 4). By this connection, in the indwelling needle 11 in the first state, the operation member 8 is pressed by the connector main body 201 of the connector 20 to move in the distal direction to a forward shifted position, penetrating the valve element 7 so that the side hole(s) 83 is distal of the valve element (opening/closing section) while the proximal end of the operation member 8 is positioned proximal of the valve element (opening/closing section). As a result of this, the indwelling needle 11 is set in the second state.

[5] Next, supply of the infusion liquid Q is started. As a result, the infusion liquid Q having flowed sequentially through the inside of the connector main body 201 and the inside of the operation member 8 is divided into a portion which flows out through the distal opening 85 of the operation member 8 and a portion which flows out through the side holes 83 (see FIG. 5). The infusion liquid Q having flowed out through the side holes 83, while pushing out the blood R in the dead space 313, joins the infusion liquid Q having flowed out through the distal opening 85 at the tapered section 312 of the flow path 31. Eventually, the entire flow path 31 is filled up with the infusion liquid Q (is primed) (see FIG. 6).

In addition, through the just-mentioned process, the blood in the dead space 313 is replaced by the infusion liquid Q as above-mentioned. Consequently, the blood R can be securely prevented from left stagnating in the dead space 313.

Figure 9:
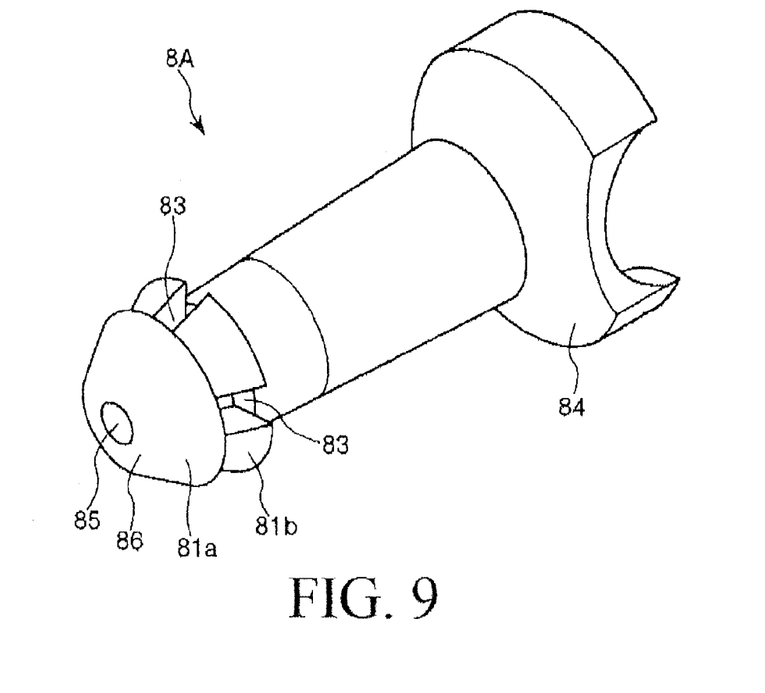
FIG. 9 is a perspective view of an operation member (second embodiment) possessed by the indwelling needle assembly.

FIG. 9 illustrates an alternative operation member which can be used with the indwelling needle assembly disclosed here.

Set forth below is a description of a second embodiment of the indwelling needle and the indwelling needle assembly disclosed here using the operation member shown in FIG. 9. The following description will primarily describe differences between this embodiment and the above-described embodiment. Features in this embodiment which are the same as in the earlier embodiment are identified by common reference numerals, and a detailed description of such features is not repeated.

The present embodiment is the same as the above-described first embodiment, except for a difference in the number of side holes formed in the operation member.

In the operation member 8A shown in FIG. 9, four side holes 83 are formed which are arranged at regular intervals along the circumferential direction of the operation member 8A. As a result, the quantity of the infusion liquid Q flowing out into the dead space 313 is increased, so that the blood R in the dead space 313 can be replaced with the infusion liquid Q more assuredly.

Figure 10:
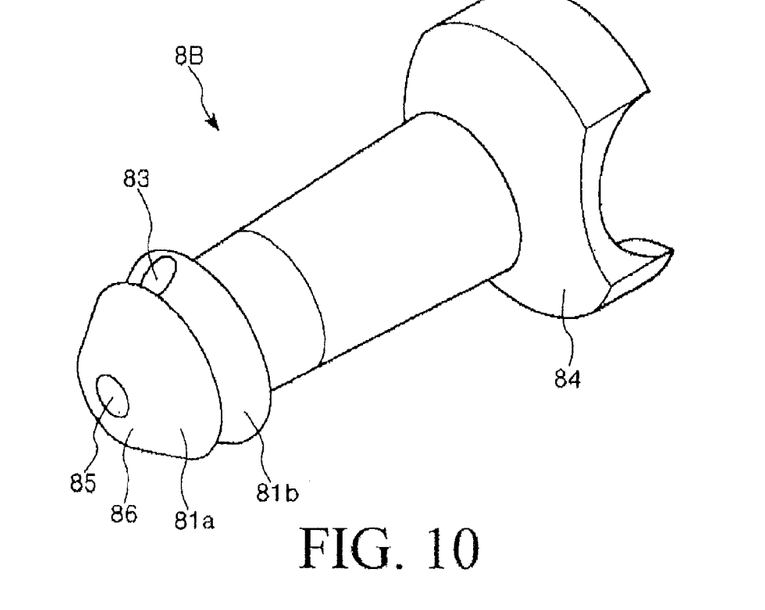
FIG. 10 is a perspective view of an operation member (third embodiment) possessed by the indwelling needle assembly.

FIG. 10 illustrates another operation member which can be used with the indwelling needle assembly disclosed here.

Set forth below is a description of a third embodiment of the indwelling needle and the indwelling needle assembly disclosed here using the operation member shown in FIG. 10. The following description will primarily describe differences between this embodiment and the above-described embodiments. Features in this embodiment which are the same as in the earlier embodiments are identified by common reference numerals, and a detailed description of such features is not repeated.

The present embodiment is the same as the above-described first embodiment, except for a difference in the shape of the side hole in side view.

In the operation member 8B shown in FIG. 10, side holes 83 are each circular in shape in side view. Also in the case where the side holes 83 are thus circular in shape, the same effect as above-mentioned (more assured replacement of the blood R in the dead space 313 by the infusion liquid Q) is obtained.

Figure 11:
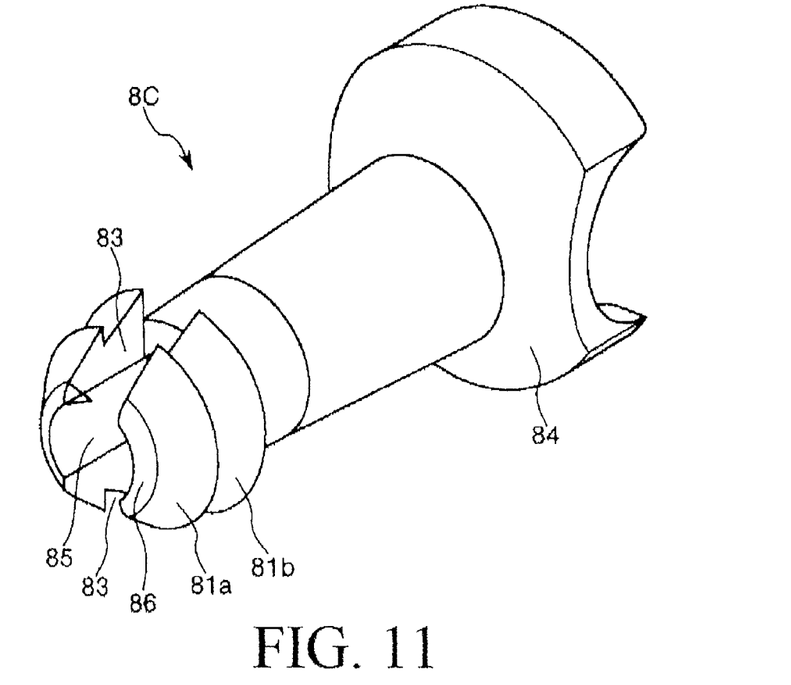
FIG. 11 is a perspective view of an operation member (fourth embodiment) possessed by the indwelling needle assembly.

FIG. 11 illustrates a further operation member which can be used with the indwelling needle assembly disclosed here.

Set forth below is a description of a fourth embodiment of the indwelling needle and the indwelling needle assembly disclosed here using the operation member shown in FIG. 11. The following description will primarily describe differences between this embodiment and the above-described embodiments. Features in this embodiment which are the same as in the earlier embodiments are identified by common reference numerals, and a detailed description of such features is not repeated.

The present embodiment is the same as the above-described first embodiment, except for a difference in the form of formation of side holes in the operation member.

The operation member 8C shown in FIG. 11 includes side holes 83 each opening also to the distal end surface 86 of the operation member 8. In other words, the side holes 83 are each communicating with the distal opening 85. Even if distal movement of the operation member 8 due to connection of the connector 20 is small and the distal end of the operation member 8 protrudes from the valve element 7 only slightly, the side holes 83 are each exposed into the flow path 31, so that the blood R in the dead space 313 can be replaced by the infusion liquid assuredly.

Figure 12:
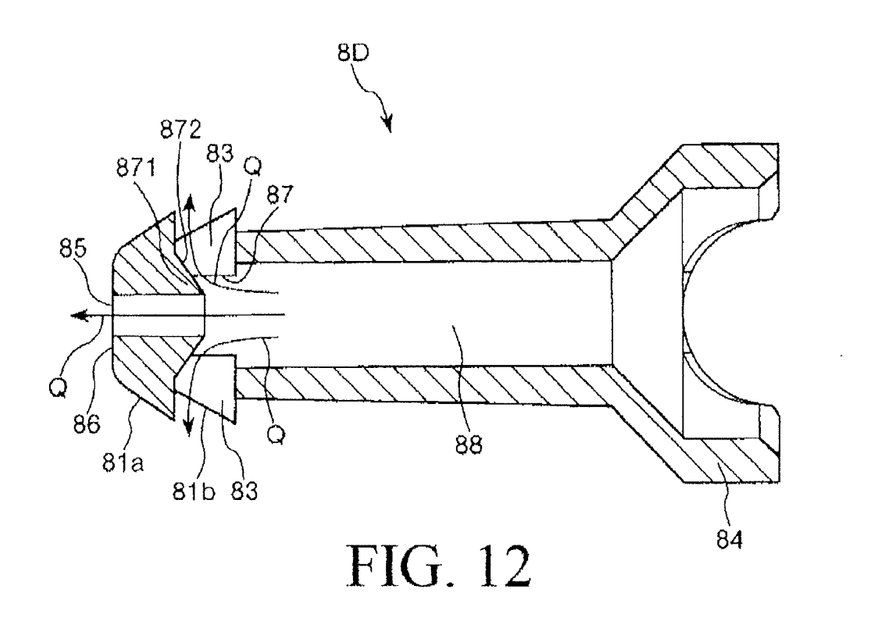
FIG. 12 is a longitudinal sectional view of an operation member (fifth embodiment) possessed by the indwelling needle assembly.

FIG. 12 illustrates a further operation member which can be used with the indwelling needle assembly disclosed here.

Set forth below is a description of a fifth embodiment of the indwelling needle and the indwelling needle assembly disclosed here using the operation member shown in FIG. 12. The following description will primarily describe differences between this embodiment and the above-described embodiments. Features in this embodiment which are the same as in the earlier embodiments are identified by common reference numerals, and a detailed description of such features is not repeated.

The present embodiment is the same as the above-described first embodiment, except for a difference in the shape of the stepped part (auxiliary part) of the operation member.

In an operation member 8D shown in FIG. 12, the stepped part 871 is formed with a slant surface 872. The slant surface 872 is slanted relative to the center axis of the operation member 8D. This helps ensure that a portion of the infusion liquid Q having flowed down through an inner cavity portion (the inside) of the operation member 8 collides on the slant surface 872, whereby the direction of the flow is easily changed to the sides of the side holes 83. Then, the infusion liquid Q of which the flow direction has thus been changed can flow out through the side holes 83 more assuredly.

While the indwelling needle and the indwelling needle assembly disclosed here have been described referring to the embodiments shown in the drawings, the invention is not restricted to these embodiments. Each of the parts constituting the indwelling needle and the indwelling needle assembly can be replaced by part(s) which can exhibit the same or equivalent function of the original part. And additional features can be added.

In addition, the indwelling needle and the indwelling needle assembly disclosed here may each be a combination of two or more configurations (features) of the above-described embodiments.

The disclosure here is not only applicable to indwelling needle assemblies (indwelling needles) used by being inserted into a blood vessel, but also to needles and needle assemblies used by being inserted into, for example, abdominal cavity, thoracic cavity, lymphatic vessel, spinal canal or the like.

In addition, the valve element (opening/closing section) is not restricted to the one having the configuration shown in the drawings, and may, for example, be one composed of a duckbill valve.

The number of the side holes formed in the operation member is not limited to two or four, and may be, for example, one, three, or five or more.

In addition, the side holes have preferably been subjected to a hydrophilicity-imparting treatment. This helps ensure that the liquid having flowed down from the connector is guided to the side holes.

The indwelling needle disclosed here includes: a hollow outer needle; a hub which is provided at a proximal end of the outer needle, has a flow path communicating with the inside of the outer needle and can connect a tube body to the flow path; and a valve mechanism which closes and opens the flow path, wherein the valve mechanism is provided with a valve element which is provided at an intermediate portion of the flow path and has an opening/closing section, which can be opened and closed, formed from an elastic material, and an operation member which operates the opening/closing of the opening/closing section, is tubular in shape and has at least one side hole penetrating a tube wall thereof; the valve mechanism can take a first state in which the opening/closing section is closed and the operation member is located on the proximal side relative to the opening/closing section, and a second state in which the operation member penetrates through the opening/closing section to protrude therefrom and the side hole is located on the distal side relative to the opening/closing section, as a result of a distal movement of the operation member pressed by the tube body upon connection of the tube body to the flow path starting from the first state; and when a liquid is supplied from the tube body in the second state, the liquid flows out from the inside of the operation member into the flow path through the side hole, and that part of the flow path which is surrounded by a wall portion defining the flow path and an outer circumferential portion of a protruding part of the operation member protruding from the opening/closing section is filled with the liquid having flowed out through the side hole. In the process of using this indwelling needle, blood flows into the flow path in the hub by flashback, and, thereafter, the flow path is primed with a liquid. In this case, the blood might be left stagnating in the flow path, especially in that part of the flow path which is surrounded by a wall portion defining the flow path and an outer circumferential portion of the protruding part of the operation member protruding from the opening/closing section of the valve body. However, the liquid can flow out into the flow path also through the side hole formed in the protruding part of the operation member, and the blood left stagnating in the just-mentioned part is replaced, so that stagnation of the blood can be securely prevented.

The detailed description above describes features and aspects of embodiments of an indwelling needle and an indwelling needle assembly. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

The invention claimed is:

1. An indwelling needle comprising:

a hollow outer needle possessing an inside;

a hub provided at a proximal portion of the outer needle, having a flow path communicatable with the inside of the outer needle and configured to connect a tube body to the flow path;

a valve mechanism which closes and opens the flow path, the valve mechanism including: a valve element provided at an intermediate portion of the flow path, the valve element being made of elastic material and having an opening/closing section which can be opened and closed; and an operation member which operates the opening and closing of the opening/closing section, the operation member possessing a tubular shape and having a distal opening and a plurality of side holes arranged circumferentially along the operation member and penetrating a wall of the operation member;

the valve mechanism being positionable in a first state in which the opening/closing section is closed and the operation member is located proximally relative to the opening/closing section, and being positionable in a second state in which the operation member penetrates through the opening/closing section such that a protruding part of the operation member protrudes from the opening/closing section;

the protruding part including the side holes, the side holes being located distally relative to the opening/closing section, as a result of distal movement of the operation member pressed by the tube body upon connection of the tube body to the flow path starting from the first state; and when a liquid is supplied from the tube body in the second state, the liquid flows out from the inside of the operation member into the flow path through both the distal opening and the plurality of side holes, and a part of the flow path which is surrounded by a wall portion of the outer needle hub and an outer circumferential portion of the protruding part of the operation member protruding from the opening/closing section is filled with the liquid having flowed out through the side hole;

wherein the operation member includes an engagement section engageable with the opening/closing section of the valve mechanism such that the valve mechanism can be maintained in the second state and proximal movement of the operation member is prevented, wherein the engagement section includes a distal enlarged diameter section, a proximal enlarged diameter section, and a body section extending therebetween;

wherein the distal enlarged diameter section has an inside diameter smaller than an inside diameter of the body section and the distal opening of the operation member has an inside diameter smaller than the inside diameter of the distal enlarged diameter section; and wherein the side holes are located on the distal enlarged diameter section.

2. The indwelling needle according to claim 1, wherein the side holes are in fluid communication with the distal opening of the operation member.

3. The indwelling needle according to claim 1,
wherein the distal opening opens in a distal-most end surface of the operation member, and each said side hole has an aperture diameter of not less than 10% of an inside diameter of the distal opening of the operation member.

4. The indwelling needle according to claim 1, wherein each said side hole has an area of not less than 0.04 mm$^2$.

5. The indwelling needle according to claim 1, wherein the operation member has an auxiliary part which assists movement toward the side hole of the liquid which has passed through the inside of the operation member.

6. The indwelling needle according to claim 1, wherein the opening/closing section is comprised of a plate-shaped part, and a through-hole penetrating the plate-shaped part in a thickness direction of the plate-shaped part.

7. A indwelling needle assembly comprising:
the indwelling needle according to claim 1;
an inner needle which is inserted in the outer needle when the indwelling needle is in the first state; and
wherein blood flows through the outer needle into the flow path when the inner needle punctures a living body surface.

8. The indwelling needle according to claim 1, wherein the proximal enlarged diameter section has an inside diameter larger than the inside diameter of the body section.

9. An indwelling needle comprising:
a hollow outer needle possessing an inside;
a hub connected to a proximal portion of the outer needle and extending proximally beyond a proximal-most end of the outer needle, the hub possessing an open proximal end to receive a portion of a tube body, the hub including a flow path surrounded by a wall of the hub and fluidly communicatable with the inside of the outer needle;
a valve element positioned in the hub at an intermediate portion of the flow path;
an operation member possessing a distal end, a proximal end, an outer circumferential surface and a through hole extending throughout the operation member from a distal opening which opens to the distal end of the operation member and a proximal opening which opens to a proximal end of the operation member, the operation member also including a side hole communicating with the through hole and opening to the outer circumferential surface of the operating member;
the valve element being made of elastic material and including an openable and closable opening/closing section;
the operation member being positioned inside the hub in an initial position so that the side hole of the operation member is located proximally of the valve element;
the opening/closing section being in a closed state when the operation member is positioned inside the hub in the initial position;
the operation member in the initial position in the hub being movable to a forward shifted position, when the portion of the tube body is positioned in the hub, in which the operation member moves toward the valve element and passes through the opening/closing section to the forward shifted position so that the side hole of the operation member is distal of the opening/closing section while the proximal end of the operation member is proximal of the opening/closing section to permit liquid introduced into the proximal opening of the through hole from the tube body to flow along the through hole and to flow out of the through hole by way of both the distal opening and the side hole so that the liquid flowing out of the side hole fills a part of the flow path surrounded by a portion of the wall of the hub and the outer circumferential surface of a part of the operation member protruding distally beyond the opening/closing section;

wherein the operation member includes a plurality of circumferentially spaced apart side holes each of which communicates with the through hole and opens to the outer circumferential surface of the operation member;

wherein the operation member includes an engagement section engageable with the opening/closing section of the valve element such that the operation member can be maintained in the forward shifted position and further proximal movement of the operation member is prevented, and wherein the engagement section includes a distal enlarged diameter section, a proximal enlarged diameter section, and a body section extending therebetween;

wherein the distal enlarged diameter section has an inside diameter smaller than an inside diameter of the body section and the distal opening of the operation member has an inside diameter smaller than the inside diameter of the distal enlarged diameter section; and the side holes are located on the distal enlarged diameter section.

10. The indwelling needle according to claim 9, wherein the side hole also opens to a distal-most end surface of the operation member.

11. The indwelling needle according to claim 9, wherein each side hole possesses an aperture diameter of not less than 10% of an inside diameter of the distal opening which opens to the distal end of the operation member.

12. The indwelling needle according to claim 9, wherein each side hole has an area of not less than 0.04 mm$^2$.

13. The indwelling needle according to claim 9, wherein the through hole in the operation member includes a stepped part at a distal end portion of the through hole, the stepped part providing a reduced inner diameter part which assists movement toward the side hole of the liquid pass through the through hole in the operation member.

14. The indwelling needle according to claim 9, wherein the opening/closing section is comprised of a plate-shaped part, and a slit penetrating through the plate-shaped part in a thickness direction of the plate-shaped part.

15. A indwelling needle assembly comprising:
the indwelling needle according to claim 9;
an inner needle which is inserted in the outer needle when the indwelling needle is in the first state; and
wherein blood flows through the outer needle into the flow path when the inner needle punctures a living body surface.

16. A method of using an indwelling needle comprising:
puncturing skin of a living body with an inner needle positioned inside a hollow outer needle, the hollow outer needle being connected a hub having a flow path, and a valve element positioned at an intermediate portion of the flow path, the valve element having an opening/closing section through which the inner needle extends so that a portion of the inner needle is on a distal side of the valve element and a portion of the inner needle is on a proximal side of the valve element;

positioning the outer needle, following the puncturing of the skin of the living body with the inner needle, to penetrate the skin of the living body so that blood from the living body flows into the flow path of the hub by way of a space between an inner surface of the outer needle and an outer surface of the inner needle;

removing the inner needle from within the outer needle, with the opening/closing section of the valve element automatically closing upon removal of the inner needle;

moving a tubular operation member positioned in the hub in a forward direction toward the valve member, the tubular operation member possessing a distal opening, a protruding part including a distal enlarged diameter section, and a side hole located at the distal enlarged diameter section which opens to an outer circumferential surface of the operation member and which communicates with an inside of the tubular operation member, a proximal enlarged diameter section, and a body section extending therebetween, the distal enlarged diameter section having an inside diameter smaller than an inside diameter of the body section and the distal opening of the operation member having an inside diameter smaller than the inside diameter of the distal enlarged diameter section;

continuing to move the tubular operation member in the forward direction so that the tubular operation member penetrates through the opening/closing section;

stopping the movement of the tubular operation member in the forward direction when the side hole is positioned distally of the opening/closing section and while a proximal end of the tubular operation member is proximal of the opening/closing section;

engaging the tubular operation member with the opening/closing section of the valve element and preventing movement of the tubular operation member in a rearward direction; and introducing liquid into the inside of the tubular operation member through a proximal opening at the proximal end of the operation member, with the liquid flowing through the distal opening and at least some of the liquid flowing into the side hole and flowing out of the side hole at the outer circumferential surface of the tubular operation member so that a part of the flow path surrounded by a wall portion defining the flow path and an outer circumferential portion of a protruding part of the operation member protruding distally from the opening/closing section is filled with the liquid which has flowed out through the side hole.

17. The method according to claim 16, wherein the tubular operation member includes a plurality of side holes and at least a part of the liquid inside the tubular operation member flows through the plurality of side hole and flows out of the side holes at the outer circumferential surface of the tubular operation member.

18. The method according to claim 16, wherein the tubular operation member includes a distal opening at the distal end of the tubular operation member, and at least some of the liquid introduced into the inside of the tubular operation member flows through the distal opening.

19. The method according to claim 16, wherein the side hole also opens to the distal end of the tubular operation member so that at least some of the liquid also flows through the side wall at the distal end of the tubular operation member.

* * * * *